Figure 1:
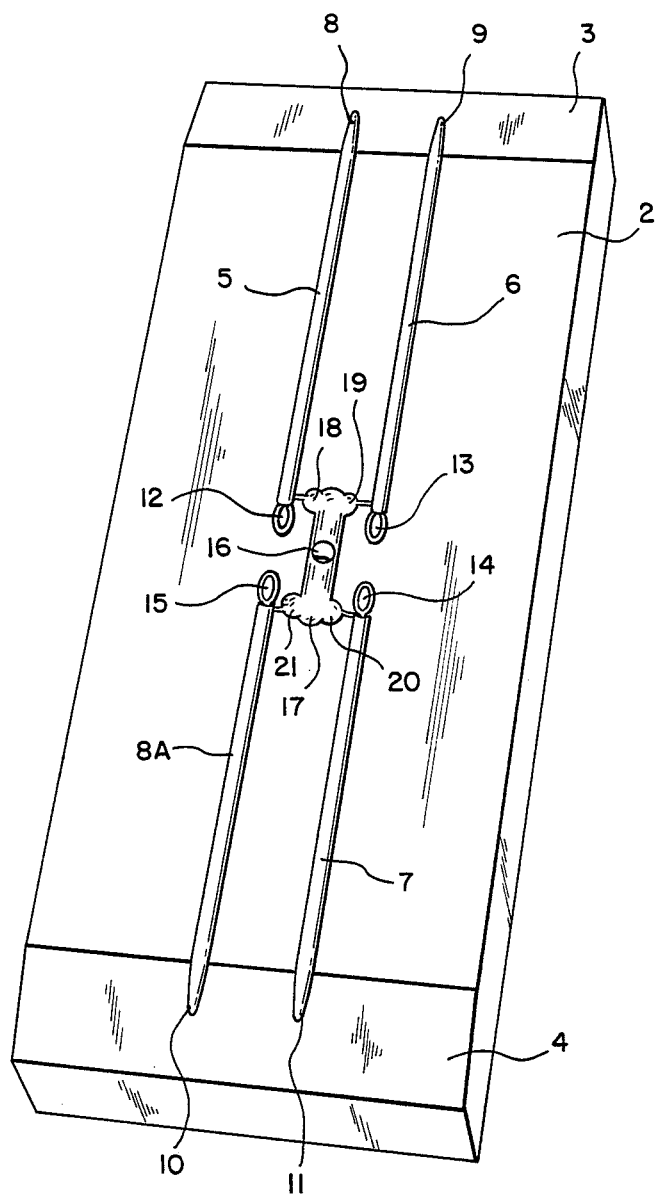

United States Patent [19]

Fransson et al.

[11] Patent Number: 4,756,864
[45] Date of Patent: Jul. 12, 1988

[54] METHOD OF MANUFACTURING AN INSTRUMENT FOR USE IN REMOVING SMALL PARTICLES

[76] Inventors: Otto Fransson; Björn Fransson, both of Postlåda 2632, 713 00 Nora, Sweden

[21] Appl. No.: 851,583

[22] Filed: Apr. 14, 1986

[30] Foreign Application Priority Data

May 30, 1985 [SE] Sweden .................................. 8502663

[51] Int. Cl.⁴ ............................................. B29C 45/00
[52] U.S. Cl. ............................. 264/328.1; 264/297.2; 425/588; 425/812
[58] Field of Search ................... 264/275, 297.2, 297.8, 264/328.12, 328.8, 537, 328.1, 328.9; 425/129 R, DIG. 812, 588; 249/95; 128/1.4, 304

[56] References Cited

U.S. PATENT DOCUMENTS

| | | | |
|---|---|---|---|
| 2,378,586 | 6/1945 | Schultz | 425/812 |
| 2,435,505 | 2/1948 | Morin | 264/328.9 X |
| 2,453,739 | 11/1948 | Bates | 264/328.9 |
| 3,899,564 | 8/1975 | Kessler et al. | 264/275 X |
| 4,254,065 | 3/1981 | Ratkowski | 264/328.8 X |
| 4,378,811 | 4/1983 | Levitan | 128/304 X |
| 4,600,008 | 7/1986 | Schmidt | 128/304 X |

Primary Examiner—Jan H. Silbaugh
Assistant Examiner—Mary Lynn Fertig
Attorney, Agent, or Firm—Dennison, Meserole, Pollack & Scheiner

[57] ABSTRACT

An instrument (22 and 23) for removing irritating particles from the eye, for instance, consists of a tubular rod provided at one end with a flexible eye or loop clamped therein. The object of the invention is to simplify manufacture of such an instrument by supplying liquid plastic to a moulding tool (1), both rod (22) and eye or loop (23) being formed as a single, coherent unit.

1 Claim, 3 Drawing Sheets

METHOD OF MANUFACTURING AN INSTRUMENT FOR USE IN REMOVING SMALL PARTICLES

The present invention relates to an instrument for removing small particles lodged in the eye. Such instruments are described in two British Patents, the first No. 12 147 from 1906 and the other No. 264 272. Such an instrument is also described in Swiss Pat. No. 239 112. All three patents show that the two ends of the loop must be manually secured in a rod. Such method of manufacture is both expensive and time-consuming. The instrument is not liimited only to removing particles from the eye. It also has innumerable applications both within the medical profession and in industry. The instrument may also be helpful in a beauty care in connection with eyelashes.

The object of the present invention is to manufacture instruments of the type described above in which the step of securing a loop at one end of the rod is eliminated. According to the invention, this can be achieved by means of injection-moulding with the aid of a tool having one or more cavities, each forming a complete instrument. According to the invention a large number of instruments can be injection-moulded simultaneously.

It has proved advantageous to supply liquid plastic to a cavity at or close to the point where the end of the tool is formed which is to be provided with a loop.

A suitable plastic according to the invention is a thermoplastic which is a polymerized acetal resin.

Further characteristics of the present invention are revealed in the following claims.

Figure 2:
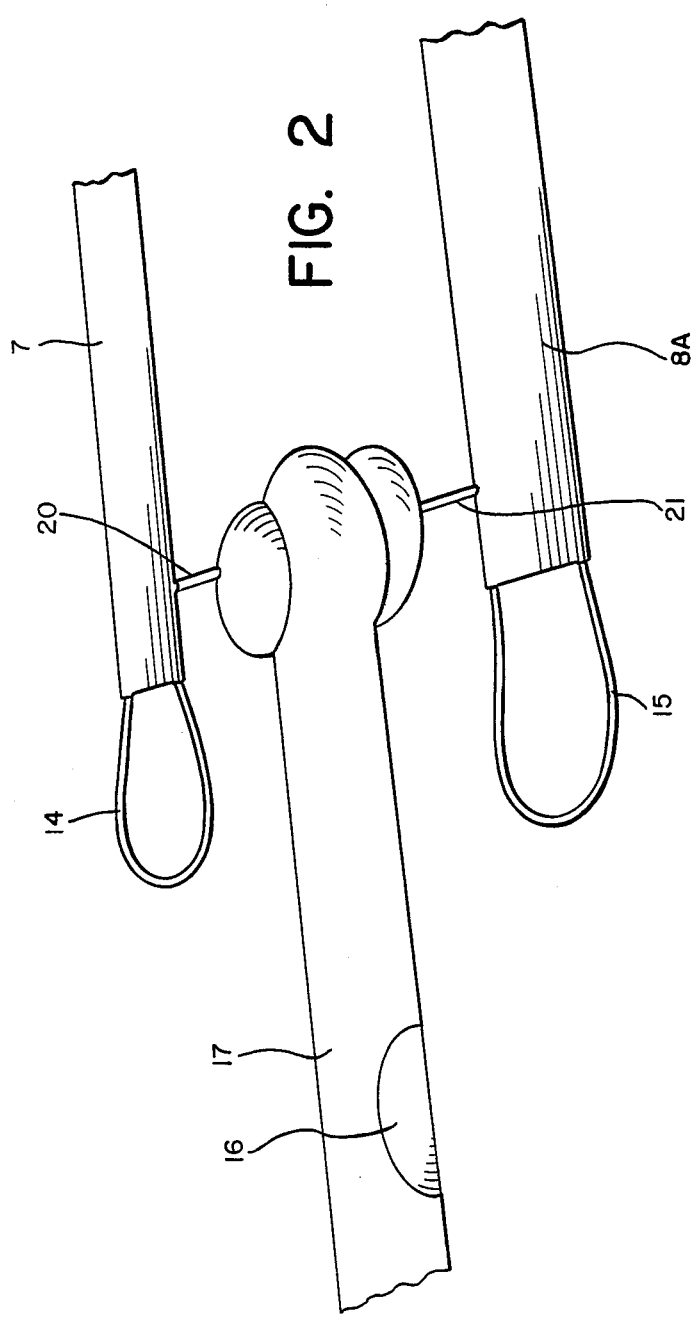
Figure 3:
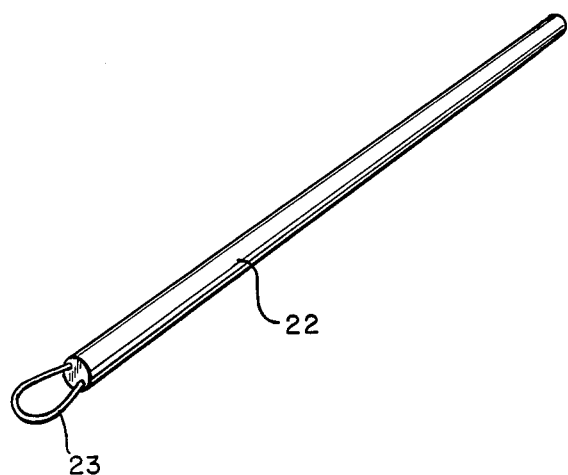

The invention will be described in more detail with reference to the accompanying three sheets of drawings in which FIG. 1 shows one half of a tool for producing the instrument pertaining to the present invention, FIG. 2 shows an enlargement of a part of the tool according to FIG. 1, and FIG. 3 shows an instrument according to the present invention.

FIGS. 1 and 2 show one half of the tool. This half is designated 1 and consists of a flat surface and two bevelled sections 3 and 4, one at each end of the tool. Four grooves 5, 6, 7 and 8A are milled in the flat surface 2. The inner surface of these grooves corresponds to half the outer surface of a rod 22. Four looped grooves 12, 13, 14 and 15 are milled in the flat surface communication with the grooves 5, 6, 7 and 8, respectively and the inner surface of these looped grooves corresponds to half the outer surface of the eye to be formed. The grooves 5 to 11 extend to the points 8 to 11 in the bevelled sections 3 and 4. This is to allow for removal of any air present in grooves 5, 6, 7, and 8A when two tool halves are fitted together. In the middle of the flat area is an inlet opening 16 for liquid plastic. The opening communicates with one half of a distribution chamber 17. Two grooves 18 and 19 extend at one end of the distribution chamber 17 and two grooves 20 and 21 at the other end. Together with corresponding grooves in the other tool-half, these form flow channels allowing liquid plastic to the cavities which are to form the rods and eyes. The outlets of grooves 18, 19 and 20, 21 are located very close to the part of each cavity where the eye is to be formed at the end of the rod.

Two identical tool halves in accordance with FIG. 1 are fitted together and a tool with four moulds is thus ready for the manufacture of four rods with eyes. The pressure on two tool halves varies between 40 and 25 ton and a gap of 0.03 mm is formed between the two halves at the bevelled sections 3 and 4. Each mould for an individual instrument has a diameter of about 2.1 mm at the eye-forming part and a diameter of 1.6 mm at the other end. Each eye-mould produces an eye with a thickness of 0.2 mm. Each eye has a diameter of about 5 mm. The plastic supplied to the four moulds through the inlet opening 16 consists of a cured resin consisting of polymerized acetal resin or of a thermoplastic having similar properties. An example of a suitable plastic is Hostaform ® with the designation 13202-1. The plastic is supplied to the moulding tool at a temperature of about 210° C. and a pressure of 80 bar. Any air enclosed in the four moulds can escape through the gap formed by the two bevelled ends of the tool halves, the opening being 0.03 mm.

Each eye in an instrument has properties enabling it to adjust to the contours of the body from which the loop is to remove an unwanted particle. When the instrument is not in use the loop returns to a predetermined initial position.

The instrument is primarily intended for removing foreign particles from an eye and the loop thus follows the curved contours of the eye. However, it is now double evident that the instrument according to the invention has inumerable applications in many different situations where the position of a particle is to be influenced.

It is advisable to make the loop sufficiently wide for a film of liquid to be formed within its confines when removing particles from an eye.

What is claimed is:

1. A method of manufacturing a unitary instrument for removing foreign bodies from the eye comprising the steps of forming a pair of complementary mold halves, each half including a recess which in combination with the other half defines at least one cavity configured to produce said instrument as a single coherent unit, said instrument including a rod portion and integral looped eye portion, said looped eye portion being of relatively thin construction on the order of 0.2 mm in thickness and defining an eye diameter of about 5 mm, connecting a source of thermoplastic material in liquid form to said cavity, forcing said liquid plastic into the portion of said cavity defining said rod portion adjacent the portion of said cavity defining the intersection of said rod and said loop, and venting said cavity at the end of said rod portion opposite said loop.

* * * * *